United States Patent
Heemstra

(10) Patent No.: US 8,945,838 B2
(45) Date of Patent: *Feb. 3, 2015

(54) APTAMER-BASED LATERAL FLOW ASSAY AND ASSOCIATED METHODS

(71) Applicant: University of Utah Research Foundation, Salt Lake City, UT (US)

(72) Inventor: Jennifer M. Heemstra, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/894,161

(22) Filed: May 14, 2013

(65) Prior Publication Data

US 2014/0011193 A1    Jan. 9, 2014

Related U.S. Application Data

(60) Provisional application No. 61/662,281, filed on Jun. 20, 2012.

(51) Int. Cl.
    *C12Q 1/68* (2006.01)
    *G01N 33/53* (2006.01)

(52) U.S. Cl.
    CPC ................................. *G01N 33/5308* (2013.01)
    USPC ....................................................... 435/6.1

(58) Field of Classification Search
    None
    See application file for complete search history.

(56) References Cited

U.S. PATENT DOCUMENTS

| | | |
|---|---|---|
| 7,799,554 B2 | 9/2010 | Mazumdar et al. |
| 2006/0019406 A1 | 1/2006 | Wei et al. |
| 2006/0068500 A1 | 3/2006 | Wei et al. |
| 2006/0166222 A1 | 7/2006 | Lu et al. |
| 2009/0030054 A1 | 1/2009 | Warmington et al. |
| 2013/0065224 A1 | 3/2013 | Lu et al. |
| 2013/0164739 A1 | 6/2013 | Heemstra |

OTHER PUBLICATIONS

Glynou et al.; "Oligonucleotide-Functionalized Gold Nanoparticles as Probes in a Dry-Reagent Strip Blosensor for DNA Analysis by Hybridization," Analytical Chemistry; Jul. 15, 2003; pp. 4155-4160; vol. 75 No. 16; ACS Publications.
Liu, et al.; "A Simple and Sensitive 'Dipstick' Test I Serum Based on Lateral Flow Separation of Aptamer-Linked Nanostructures;" Angew. Chem. Int. Ed. 2006; vol. 45; pp. 7955-7959.
Sharma, et al.; "Enzime-Linked Small-Molecule Detection using Split Aptamer Ligation"; Analytical Chemistry; published Jun. 18, 2012; American Chemical Society; pp. 6104-6109.
Sharma, et al.; "Small-Molecule-Dependent Split Aptamer Ligation"; J. Am. Chem. Soc., 133 (32), pp. 12426-12429; published Jul. 16, 2011.
Stojanovic, et al.; "Fluorescent Sensors Based on Aptamer Self-Assembly"; J. Am. Chem. Soc. Nov. 2, 2000, vol. 122; pp. 11547-11548.
Toubanaki, et al.; "Dry-Reagent Disposable Biosensor for Visual Genotyping of Single Nucleotide Polymorphisms by Oligonucleotide Ligation Reaction: Application to Pharmacogenetic Analysis;" Human Mutation 29(8), pp. 1071-1078; published online May 9, 2008 in Wiley InterScience.
Xu, et al.; "Aptamer-Functionalized Gold Nanoparticles as Probes in a Dry-Reagent Strip Biosensor for Protein Analysis"; Analytical Chemistry, vol. 81; No. 2; Jan. 15, 2009; pp. 669-675.

*Primary Examiner* — Tracy Vivlemore
(74) *Attorney, Agent, or Firm* — Thorpe North & Western LLP

(57) ABSTRACT

Methods, assays, and products for the detection of analytes in a sample are provided. In one aspect, for example, a device for detecting an analyte in a sample can include a fluid transfer membrane further including a sample input region operable to receive a liquid sample, a reagent region including a first split aptamer segment, a second split aptamer segment, and a detection marker, where the first and second split aptamers are operable to ligate in the presence of the analyte. The detection marker is operable to bind to the second split aptamer. The device can further include a test region having an immobilized binding reagent operable to bind to the first split aptamer segment such that the detection marker is held in the test region when the first split aptamer segment is ligated to the second split aptamer segment due to the analyte being present in the sample.

18 Claims, 9 Drawing Sheets

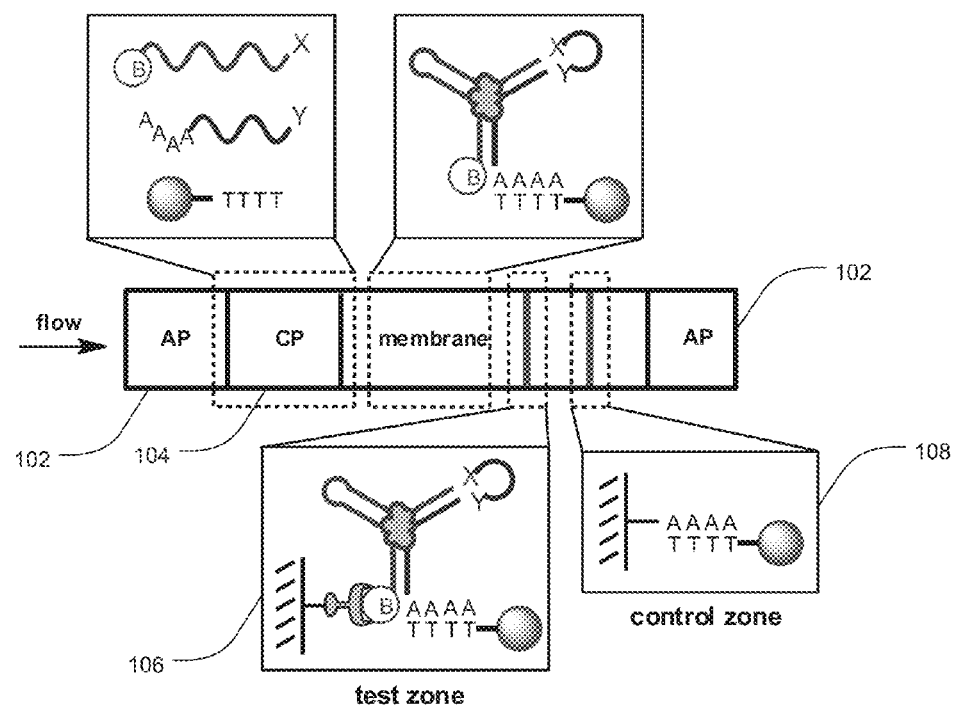
FIG. 10a
11: 5' biotin-PEG$_{18}$-GGC GAC AAG GAA AAT CCT TCA ACG AAG TGG GTC GCC-A$_{30}$
12: 5' N$_3$-GTT CTT CAA TGA AGT GGG ACG ACA-A$_{30}$
13: 5' biotin-PEG$_{18}$-GGG AGT CAA GAA C-NH$_2$
14: 5' biotin-PEG$_{18}$-GGG AGT CAA GAA C-NH-DIBAC
FIG. 10b
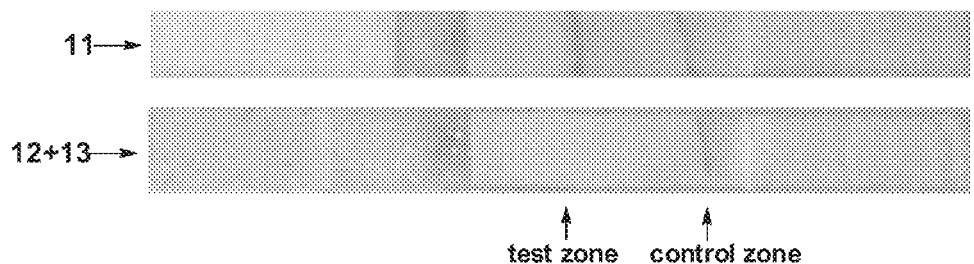
FIG. 10c

SEQUENCE LISTING

<160> NUMBER OF SEQ ID NOS: 6

<210> SEQ ID NO 1
<211> LENGTH: 13
<212> TYPE: DNA
<213> ORGANISM: Artificial Sequence
<220> FEATURE:
<223> OTHER INFORMATION: Completely Synthesized

<400> SEQUENCE: 1

```
gggagtcaag aac                                                              13

<210> SEQ ID NO 2
<211> LENGTH: 24
<212> TYPE: DNA
<213> ORGANISM: Artificial Sequence
<220> FEATURE:
<223> OTHER INFORMATION: Completely Synthesized

<400> SEQUENCE: 2
gttcttcaat gaagtgggac gaca                                                  24

<210> SEQ ID NO 3
<211> LENGTH: 21
<212> TYPE: DNA
<213> ORGANISM: Artificial Sequence
<220> FEATURE:
<223> OTHER INFORMATION: Completely Synthesized

<400> SEQUENCE: 3
taatatatga gggggtccat a                                                     21

<210> SEQ ID NO 4
<211> LENGTH: 20
<212> TYPE: DNA
<213> ORGANISM: Artificial Sequence
<220> FEATURE:
<223> OTHER INFORMATION: Completely Synthesized

<400> SEQUENCE: 4
tatggaagga ggcgatatta                                                       20

<210> SEQ ID NO 5
<211> LENGTH: 36
<212> TYPE: DNA
<213> ORGANISM: Artificial Sequence
<220> FEATURE:
<223> OTHER INFORMATION: Completely Synthesized

<400> SEQUENCE: 5
ggcgacaagg aaaatccttc aacgaagtgg gtcgcc                                     36

<210> SEQ ID NO 6
<211> LENGTH: 24
<212> TYPE: DNA
<213> ORGANISM: Artificial Sequence
<220> FEATURE:
<223> OTHER INFORMATION: Completely Synthesized

<400> SEQUENCE: 6
cttcttcaac gaagtgggac gaca                                                  24
```

APTAMER-BASED LATERAL FLOW ASSAY AND ASSOCIATED METHODS

BACKGROUND OF THE INVENTION

Molecular recognition between DNA molecules has been shown to be a powerful tool for directing and promoting various chemical reactions. DNA-templated reactions have been utilized for a wide assortment of tasks, including ligation of complementary oligonucleotides, generating encoded libraries of complex small molecules, and detecting nucleic acids and proteins. However, such DNA-templated reactions are dependent upon the sequence defined affinity of the nucleic acid strands for one another.

SUMMARY OF THE INVENTION

The present disclosure provides methods, assays, and products for the detection of analytes in a sample. In one aspect, for example, a device for detecting an analyte in a sample can include a fluid transfer membrane further including a sample input region operable to receive a liquid sample, a reagent region including a first split aptamer segment, a second split aptamer segment, and a detection marker, where the first and second split aptamers are operable to ligate in the presence of the analyte. The detection marker is operable to bind to the second split aptamer. The device can further include a test region having an immobilized binding reagent operable to bind to the first split aptamer segment such that the detection marker is held in the test region when the first split aptamer segment is ligated to the second split aptamer segment due to the analyte being present in the sample. The device can be arranged such that a sample delivered to the sample input region passes along the fluid transfer membrane through the reagent region prior to contacting the test region. In some aspects, the immobilized binding reagent can be arranged within the test region as a discrete test pattern (e.g., a test line).

In another aspect, the fluid transfer membrane can include a control region having a control binding reagent operable to bind to the second split aptamer segment. The control region can, in some cases, be positioned such that the sample contacts the test region prior to contacting the control region. In some aspects, the control binding reagent can be arranged within the control region as a discrete control pattern (e.g., a control line). In yet another aspect, the fluid transfer membrane can include a conjugation region positioned between the reagent region and the test region, where the conjugation region can allow ligation of the first and second split aptamers in the presence of the analyte prior to contacting the test region. Furthermore, in some aspects at least one of the first split aptamer, the second split aptamer, or the detection marker can be present at the test region in a dry form prior to adding the liquid sample to the sample input region.

In another aspect, a method of detecting an analyte in a sample can include applying a liquid sample to a fluid transfer membrane, and flowing the liquid sample through a reagent region including a first split aptamer segment, a second split aptamer segment, and a detection marker. The first and second split aptamers ligate together in the presence of the analyte and the detection marker binds to the second split aptamer. The method can also include flowing the liquid sample through a test region having an immobilized binding reagent selective for the first split aptamer segment such that the first split aptamer segment binds to the immobilized binding reagent and the detection marker is held in the test region when the first split aptamer segment is ligated to the second split aptamer segment due to the analyte being present in the sample. In some aspects the method can further include detecting the presence of the detection marker in the test region. In some aspects, at least one of the first or second split aptamer segments can be a nucleic acid aptamer, such as, for example, a DNA aptamer. Also, in some aspects non-limiting examples of analytes can include small molecules such as narcotics, toxins, disease biomarkers, and the like. In another aspect, the method can also include flowing the liquid sample past the test region and through a control region including a control binding reagent selective for the detection marker, where the control region is positioned such that the sample contacts the test region prior to contacting the control region. Further, in some aspects, the liquid sample can be flowed through a conjugation region positioned between the reagent region and the test region where the conjugation region may be operable to allow ligation of the first and second split aptamers in the presence of the analyte prior to contacting the test region.

In one aspect, ligating the first and second split aptamers further includes reacting together the first split aptamer segment having a first reactive group coupled thereto, the second split aptamer segment having a second reactive group coupled thereto, where the first and second split aptamer segments are collectively selective for the analyte, and a sample containing the analyte. Upon reaction, the first split aptamer segment and the second split aptamer segment bind to the analyte and the first reactive group and the second reactive group react to form an aptamer ligation product of the first split aptamer segment and the second split aptamer segment.

DEFINITIONS OF TERMS

In describing and claiming the present invention, the following terminology will be used in accordance with the definitions set forth below.

The singular forms "a," "an," and, "the" can include plural referents unless the context clearly dictates otherwise. Thus, for example, reference to "a linkage" can include reference to one or more of such linkages, and reference to "an aptamer" can include reference to one or more of such aptamers.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint without affecting the desired result.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

BRIEF DESCRIPTION OF THE DRAWINGS

FIG. 10a shows representations and data of a lateral flow assay in accordance with another embodiment of the present invention.

FIG. 10b shows representations and data of a lateral flow assay in accordance with another embodiment of the present invention.

FIG. 10c shows representations and data of a lateral flow assay in accordance with another embodiment of the present invention.

DETAILED DESCRIPTION

The present disclosure provides novel techniques for using a lateral flow assay to detect an analyte in a sample, where the analyte facilitates a chemical reaction between two aptamer strands, such as nucleic acid strands. This novel approach can utilize an aptamer-templated reaction (e.g. a DNA templated reaction) controlled by small-molecule or other analyte binding, as opposed to a binding scheme such as inherent Watson-Crick affinity between the DNA strands. The recognition element utilized to accomplish such a task is a split aptamer, which is comprised of two nucleic acid strands that bind to one another in the presence of a specific analyte target. Thus, in one aspect such a reaction can be a ligation between two fragments of a DNA split aptamer.

Utilizing a split aptamer selective for cocaine and a strain-promoted azide-alkyne cycloaddition reaction, for example, small molecule-dependent ligation that is dose-dependent over a wide range of cocaine concentrations can be achieved. Additionally, such a ligation reaction is compatible with complex biological fluids such as human blood serum. Moreover, studies of split aptamer ligation at varying salt concentrations and using structurally similar analogues of cocaine can reveal new insight into the assembly and small-molecule binding properties of the cocaine split aptamer. The ability to translate the presence of a small molecule target into a DNA ligation can be utilized as new broadly applicable small molecule detection assays. It should be noted that the sample can be any fluid capable of containing an analyte, including, without limitation, urine, blood, plasma, semen, saliva, cerebrospinal fluid, environmental water samples, food and drink samples, and the like.

Strain-promoted azide-alkyne cycloadditions are examples of reactions that can be useful because such chemistry does not significantly interfere with the small-molecule target and is compatible with complex biological fluids. Additionally, such chemistry is orthogonal to a wide assortment of functional groups and does not require additional reagents. It should be noted, however, that the present scope is not limited by the specific chemistries exemplified herein, nor is it limited by the specific exemplified small molecule species.

Figure 1:
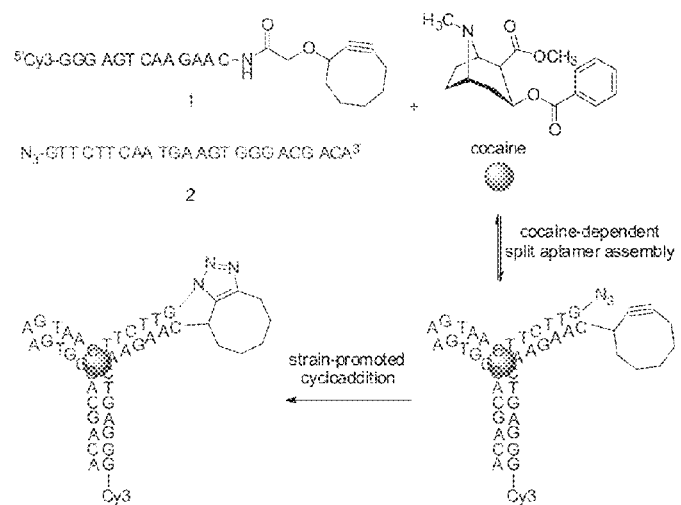
FIG. 1 is a schematic representation of a cocaine-selective DNA aptamer in accordance with one embodiment of the present invention.

In one example, as is shown in FIG. 1, a cocaine split aptamer fragment 1 (SEQ ID 001) is coupled with a cyclooctyne carboxylic acid and the other aptamer fragment 2 (SEQ ID 002) incorporates an azide. Strand 1 can additionally be functionalized with a visualization marker, such as, for example, a Cy3 fluorophore, thus enabling visualization of the ligation reaction by a suitable method such as denaturing polyacrylamide gel electrophoresis (PAGE). As can be seen in FIG. 1, cocaine directs assembly of the split aptamer fragments, thereby positioning the azide and cyclooctyne in close proximity to one another. Such proximal positioning enhances the effective molarity of the reactants and can thus accelerate the templated cycloaddition relative to the untemplated background reaction. Thus, any chemistry capable of ligation via such a proximity facilitated reaction can be similarly utilized in an analyte detection assay.

Split aptamer assembly is an equilibrium process that is dependent in part upon the concentration of the small molecule. Thus, the templated ligation should proceed in a dose-dependent manner with respect to the small molecule. In addition to the lateral flow assays described herein, denaturing PAGE can be used to monitor the reaction progress, as unligated fragments migrate farther on the gel relative to ligated fragments. Additionally, quantification of a visual marker such as Cy3 fluorescence can reveal the portion of the labeled fragment that has been incorporated into ligated product.

Figure 2:
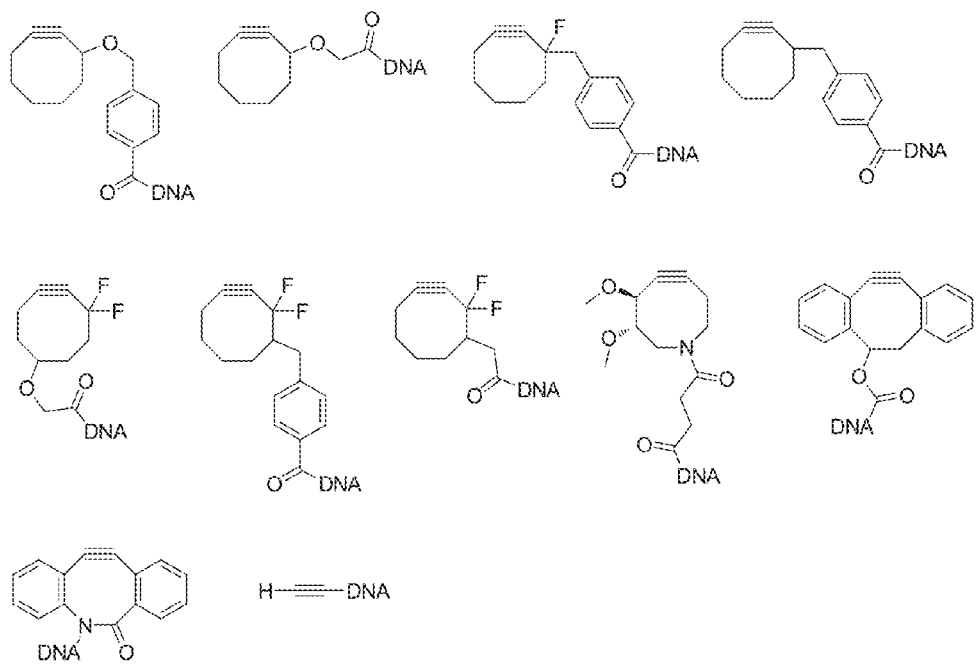
FIG. 2 shows a representation of reactive groups in accordance with another embodiment of the present invention.
Figure 3:
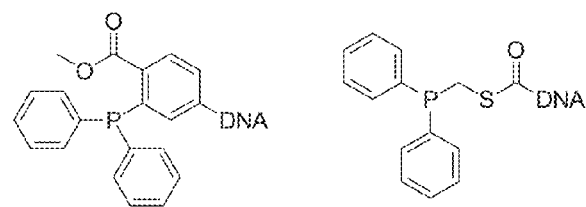
FIG. 3 shows a representation of reactive groups in accordance with another embodiment of the present invention.
Figure 4:
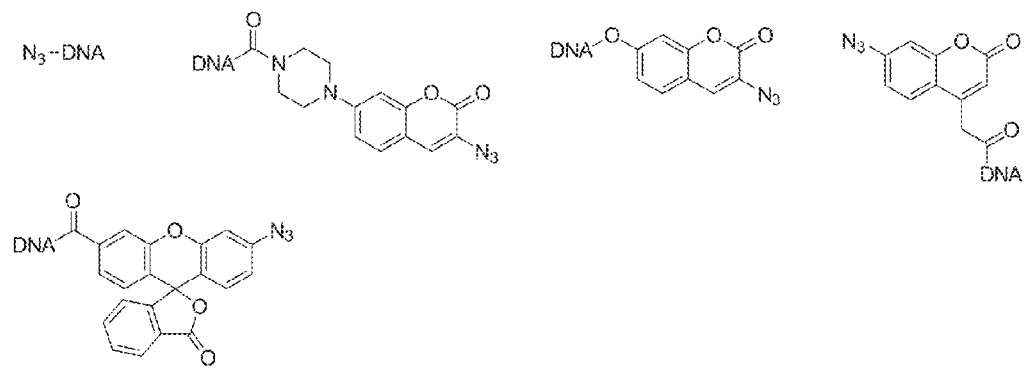
FIG. 4 shows a representation of reactive groups in accordance with another embodiment of the present invention.
Figure 5:
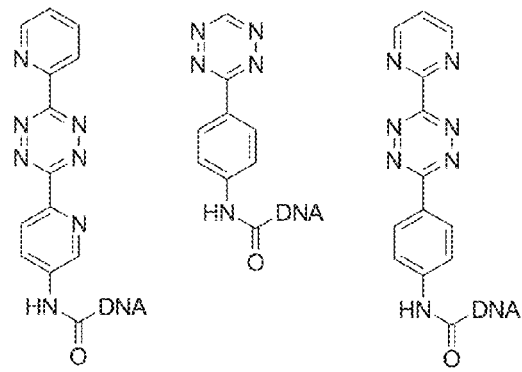
FIG. 5 shows a representation of reactive groups in accordance with another embodiment of the present invention.
Figure 6:
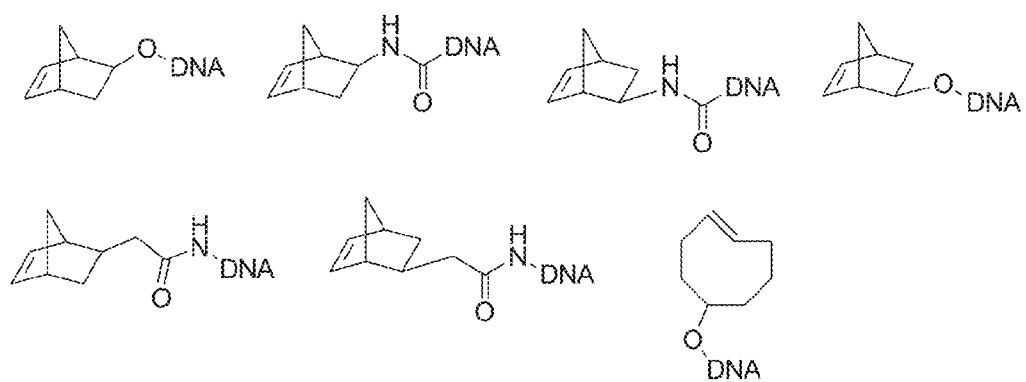
FIG. 6 shows a representation of reactive groups in accordance with another embodiment of the present invention.

As has been described, various chemistries can be utilized in ligation reactions to join split aptamers in a small molecule-dependent reaction, and any such chemistry is considered to be within the present scope. For example, in one aspect a strain-promoted azide-alkyne cycloaddition reaction between an azide and a cyclooctyne carboxylic acid can be utilized, as is described above. In other aspects, a ligation chemistry can be a reaction between an alkyne or a phosphine and an azide. Non-limiting examples of alkynes are shown in FIG. 2. Examples of phosphines are shown, without limitation, in FIG. 3. Non-limiting examples of azides are shown in FIG. 4. In another aspect, a ligation chemistry can be a reaction between a tetrazine and an alkene. Non-limiting examples of tetrazines are shown in FIG. 5, and non-limiting examples of alkenes are shown in FIG. 6.

Additionally, an aptamer can be linked to a specified reactive group, both for the ligation chemistries described above and other chemistries not exemplified, with any known technique for making such a linkage. For example, such a linkage can be made using DNA functionalized with an amine, carboxylic acid, bromide, iodide, alcohol, or thiol functional group with or without an alkane or polyethyleneglycol spacer of 3-12 atoms in length.

Figure 7:
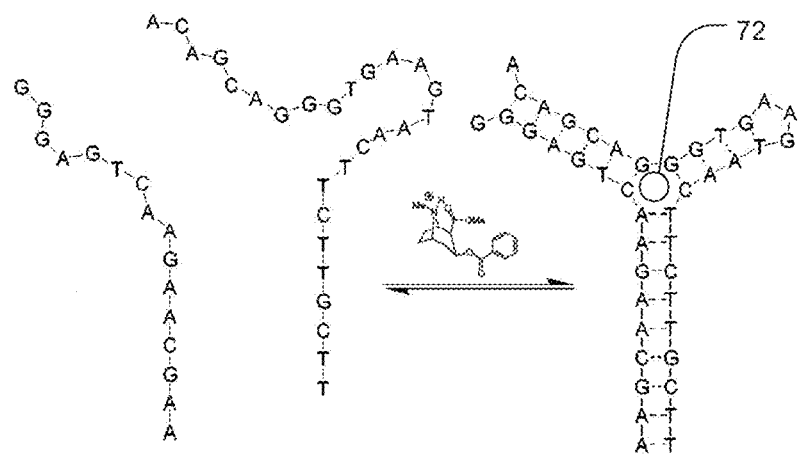
FIG. 7 shows a representation of a DNA aptamer in accordance with another embodiment of the present invention.
Figure 8:
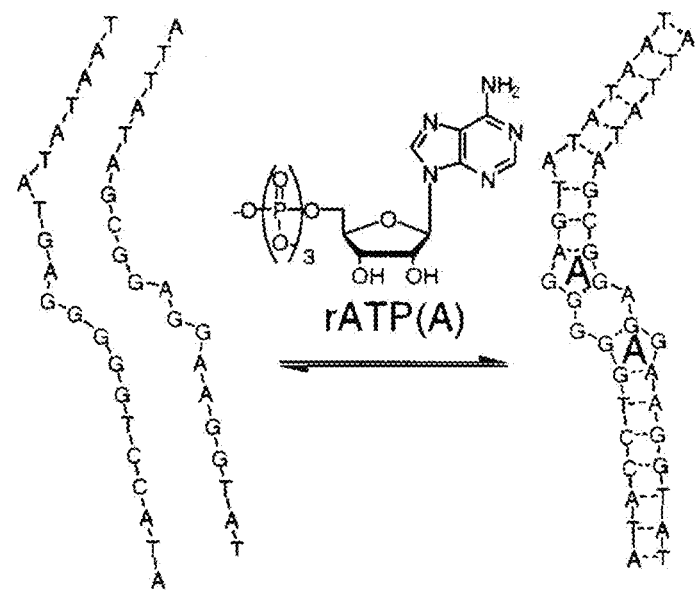
FIG. 8 shows a representation of a DNA aptamer in accordance with another embodiment of the present invention.

A variety of aptamers are contemplated for use with the present techniques, and any aptamer that shows small molecule-binding dependence is considered to be within the present scope. In other words, the present technique as described for cocaine molecules can be utilized with aptamers selective for other small molecules with potentially only minor modifications. Once in possession of the concepts disclosed herein, one skilled in the art can readily develop split aptamer assays for any small molecule to which aptamer specificity can be generated, Accordingly, the aptamers disclosed herein are meant to be merely exemplary, and should not be seen as limiting the present scope. In one aspect, for example, an aptamer can be a cocaine-selective aptamer (SEQ ID 001 left strand, SEQ ID 002 right strand), as is shown in FIG. 7, where cocaine 72 is shown bound in the aptamer. In another aspect, as is shown in FIG. 8, an aptamer can be an ATP-selective aptamer, where ATP is shown bound in the aptamer at A.

A variety of assays are contemplated for the detection of ligated aptamers, and any such assay is considered to be within the present scope. Non-limiting examples of such assays can include enzyme-linked assays, lateral flow assays, fluorometric assays, colorimetric assays, electrophoretic assays, and the like.

In one aspect, for example, a lateral flow assay can be utilized to detect ligated aptamers, and thus can be useful for the detection of an analyte in a sample. In one specific aspect, a lateral flow assay device can include a fluid transfer membrane having a sample input region operable to receive a liquid sample and a reagent region including a first split aptamer segment, a second split aptamer segment, and a detection marker that can bind to the second split aptamer segment. The sample input region and the reagent region can be a portion of the fluid transfer membrane, or one or more of these regions can be a separate structure that is in fluid communication with the fluid transfer membrane to allow passage of the liquid sample and the components of the reagent region to flow along the device. It is additionally contemplated that one or more of the first split aptamer segment, the second split aptamer segment, or the detection marker can be premixed and/or pre-incubated prior to application to the sample input region.

The first and second split aptamers thus ligate in the presence of a specific analyte, and the detection marker is specific to the second split aptamer. The device is arranged such that a liquid sample deposited at the sample input will flow along the fluid transfer membrane through the reagent region. At the reagent region, the liquid sample mixes the first split aptamer segment with the second split aptamer segment and the detection marker. The detection marker is specific to and thus binds to the second split aptamer. If the analyte is present in the sample, the first and second split aptamer segments will ligate to form a ligated aptamer.

Any spatial combination or arrangement of the components of the reagent region that allows functionality of the lateral flow assay is considered to be within the present scope. In one aspect, one or more of the components can be in discrete regions of the reagent area. For example, it can be beneficial to apply each component in discrete adjacent bands to allow the liquid sample to effectively mix the components as the liquid moves along the fluid transfer membrane. In other examples, two or more of the components can be mixed together and applied to the reagent region. This can be a homogenous mixture or a non-homogenous mixture. Additionally, it is noted that the components can be applied to the reagent region in a variety of physical forms, such as, for example, liquid form, dry form, gel form, and the like. In some aspects, components can be in different physical forms. For example, one component can be applied to the reagent region as a dry form while another component is added as a liquid.

The device can also include a test region having an immobilized binding reagent that specifically binds to the first split aptamer segment. As such, first split aptamer segments moving along the fluid transfer membrane contact the test region and are thus bound to the immobilized binding reagent. In those cases where the analyte is present in the liquid sample, the first split aptamer segment will thus be ligated to the second split aptamer segment that is in turn bound to the detection marker. As such, aptamer can be detected in the liquid sample by observing detection marker bound in the test region. The binding reagent can be bound to the test region by any technique that is compatible with a lateral flow assay. In some aspects, the binding reagent can be immobilized at the test region in a discrete pattern (i.e. a discrete test pattern). Non-limiting examples of such discrete patterns can include lines, circles, rectangles, squares, triangles, and the like. The binding reagent can also be immobilized across the test region in a non-discrete pattern.

In another aspect, the device can additionally include a control region having a control binding reagent that specifically binds to the second split aptamer segment. The control region can be positioned along the fluid transfer membrane such that the liquid sample contacts the test region prior to contacting the control region. As such, second split aptamer segments that flow by the test region can bind at the control region. In this way, the functionality of the lateral flow assay can be ascertained and verified both for samples devoid of the analyte. Additionally, in order to show such a positive control even when the analyte is present in the sample, an excess of second split aptamer segments and detection markers can be added to the regent region, thus assuring that a portion of the detection marker will reach the control region. It is also contemplated that in some aspects the control region can be positioned along the fluid transfer membrane such that the liquid sample contacts the control region prior to contacting the test region. In such cases it can be beneficial to utilize sufficient second split aptamer segment in the assay to bind to the control binding reagent and to react with the first split aptamer segment at a high enough concentration to allow detection in the test region. Devices lacking a control region are also contemplated.

The control binding reagent can be bound to the control region by any technique that is compatible with a lateral flow assay. In some aspects, the control binding reagent can be immobilized at the control region in a discrete pattern (i.e. a discrete control pattern). Non-limiting examples of such discrete patterns can include lines, circles, rectangles, squares, triangles, and the like. The control binding reagent can also be immobilized across the control region in a non-discrete pattern.

In another aspect, a conjugation region can be positioned between the reagent region and the test region to allow mixing and ligation of the first and second split aptamers in the presence of the analyte prior to contacting the test region. Additionally, the length of the conjugation region can be varied to vary the conjugation duration between the aptamer segments. For example, increasing the length of the conjugation region allows for a greater ligation time prior to contacting the test region.

Detection markers can include any known marker that is capable of being used in a lateral flow assay. Non-limiting examples can include various nanoparticles, gold nanoparticles, quantum dots, small molecule dyes, colored microbeads, and the like, including appropriate combinations thereof.

Figure 9:
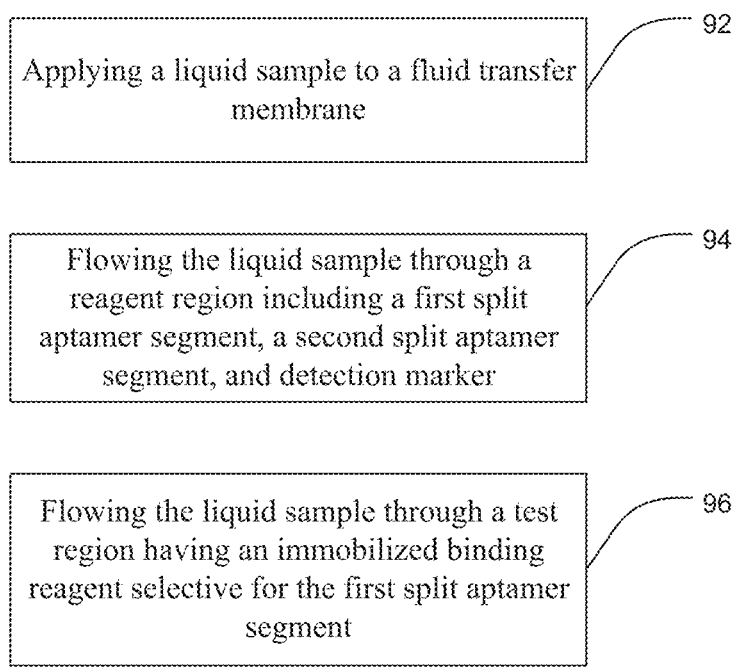
FIG. 9 shows a flow chart representation of a method of detecting an analyte in a sample in accordance with another embodiment of the present invention.

The present disclosure additionally provides methods of detecting an analyte in a sample. In many cases, the analyte can be a pre-identified analyte around which a particular split aptamer system was created. As is shown in FIG. 9, one such method can include 92 applying a liquid sample to a fluid transfer membrane and 94 flowing the liquid sample through a reagent region including a first split aptamer segment, a second split aptamer segment, and detection marker. The first and second split aptamers ligate in the presence of the analyte and the detection marker binds to the second split aptamer. The method can also include 96 flowing the liquid sample through a test region having an immobilized binding reagent selective for the first split aptamer segment such that the first split aptamer segment binds to the immobilized binding reagent and the detection marker is held in the test region when the first split aptamer segment is ligated to the second split aptamer segment due to the analyte being present in the sample.

In another aspect, the method can include flowing the liquid sample past the test region and through a control region including a control binding reagent selective for the second split aptamer segment, where the control region is positioned such that the sample contacts the test region prior to contacting the control region.

As such, a sample can be placed on a sample input region of a lateral flow device, and the presence of the analyte of interest can be ascertained by monitoring the test region of the device. If a marker appears in the test region, the analyte was present in the sample. If the marker does not appear in the test region, the analyte was not present in the sample. As an added measure, the control region should show the appearance of the detection marker to ensure that the lateral flow assay is working properly.

One specific exemplary design of an aptamer-based lateral flow sensor is shown in FIG. 10a. In this case, the lateral flow sensor can be constructed by mounting two cellulose absorbent pads (AP, 102) and one glass fiber conjugate pad (CP, 104) onto a lateral flow membrane card. Streptavidin (immobilized binding reagent) and polyA DNA (control binding reagent) can be applied onto the membrane to form the test zone (test region, 106) and control zone (control region, 108), respectively. To detect the presence of the target small molecule or other analyte, three components can be placed on the conjugate pad at a sample input region. The first component can be a first split aptamer segment having a 5' binding moiety such as biotin, and 3' cyclooctyne. The second component can be a second split aptamer segment having, for example, a 5' azide and a 3' binding region for the detection marker. The third component can be a detection marker capable of binding specifically to the 3' binding region of the second split aptamer segment. As one example, the split aptamer can have a 3' polyA tail (e.g. an A30 tail), the detection marker can be polyT DNA-functionalized gold nanoparticles (AuNP). If the target molecule or analyte is present in the sample, it will direct assembly of the two split aptamer segments, resulting in ligation to form a DNA strand having 5' biotin and 3' A30. This ligated strand will thus anneal to the polyT-AuNP and direct pull-down of the AuNP onto the streptavidin test zone to form a red test line due to the AuNP. In one specific aspect the sensor can be constructed using a stoichiometric excess of polyT-AuNP such that some AuNP will flow past the test region and bind to the polyA control region to form the control line. Thus, if the target is present both the test and control lines will be observed; if no target is present, only the control line will be observed. FIG. 10a thus shows an exemplary design of a lateral flow sensor device. FIG. 10b shows exemplary DNA sequences for aptamers that can be used for cocaine detection (strand 11—SEQ ID 005; strand 12—SEQ ID 002; strands 13 & 14—SEQ ID 001).

Thus, such a split aptamer lateral flow assay enables the detection of small-molecules and the templated ligation can be conducted at the solvent interface of the lateral flow device rather than in a sample solution. Carrying out the ligation on the lateral flow membrane enables all reagents to be preloaded onto the sensor, thus reducing the need for sample manipulation by the end user, and thus making the sensor more convenient for use in the point-of-care setting.

FIG. 10c shows results from a lateral flow assay showing DNA 11 (representing ligated aptamer) or DNA 12 and 13 (representing unligated split aptamer fragments) to the running buffer. DNA 11 resulted in visible control and test lines on the sensor, while DNA 12 and 13 provided only the control line.

Additionally, it should be noted that any analyte or molecule that is capable of being detected using the split aptamer technique is considered to be within the present scope. As has been described, various opioids can be useful analytes to test for using such lateral flow devices. For example, the cocaine split aptamer can be utilized for the detection of cocaine and related compounds in a biological sample. In one specific aspect, a lateral flow membrane used to construct the sensors can have a flow rate of about 1 cm/min. The distance between the conjugate pad and the test zone can be approximately 2 cm. Thus, the split aptamer fragments have approximately 2 min to ligate as they flow up the sensor. In solution-phase split aptamer ligation studies using DIBAC cyclooctyne, dose-dependent ligation with reaction times as short as 2 min have been observed. Thus, it is reasonable that the ligation occurring on the lateral flow membrane will proceed to a sufficient degree to enable detection of the test line.

Returning to FIG. 10b, DIBAC cyclooctyne can be appended to DNA 13 to give DNA 14, and DNA 12 and 14 can be spotted onto the conjugate pad of the lateral flow sensor. The sensors can be placed in solutions of artificial urine media containing 100 nM-1 mM cocaine, and the test solution allowed to flow to the top of the sensor. The intensity of the test line should increase with increasing cocaine concentration, while the intensity of the control line should remain relatively constant. If a visible test line in the absence of cocaine is observed, indicating significant background ligation, azide sequence 12 can be mutated to generate more specific split aptamer molecules. Conversely, if a visible test line is not observed with cocaine concentrations of 7 µM or higher, the quantity of DNA spotted onto the conjugate pad can be increased, thus increasing the concentration of DNA in solution on the membrane. Alternatively, the length of the membrane can be increased to increase the reaction time before the solvent front reaches the test zone. In some aspects, a design can be implemented in which the split aptamer fragments are pre-incubated with the test sample, and then eluted on the lateral flow sensor.

Figure 11A:
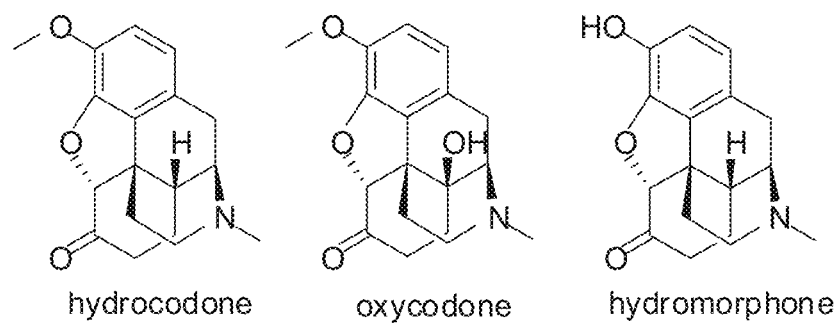
FIG. 11a shows representations of opioid and opioid-like molecules in accordance with another embodiment of the present invention.
Figure 11B:
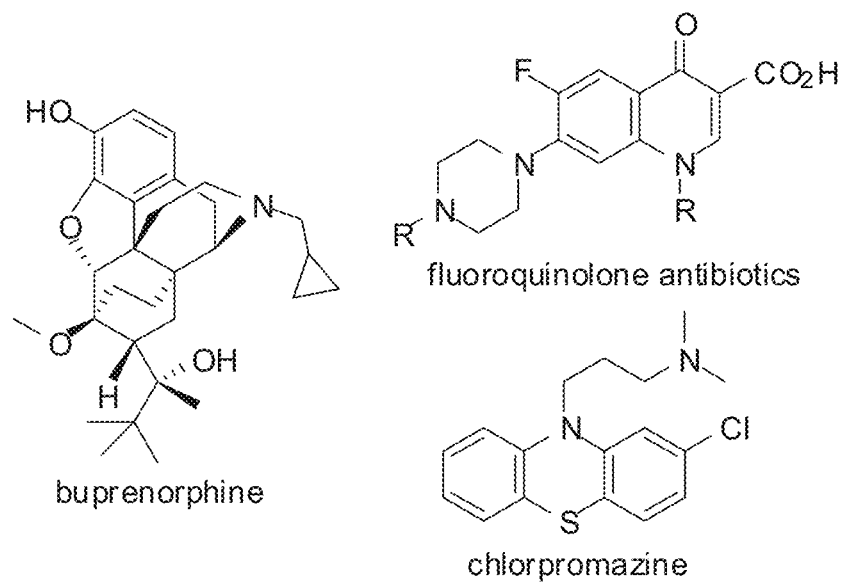
FIG. 11b shows representations of opioid and opioid-like molecules in accordance with another embodiment of the present invention.

As has been described, a variety of analytes can be detected utilizing the present techniques. In some aspects, analyte molecules that are challenging to distinguish using traditional antibody techniques can be readily identified using the present split aptamer approach. For example, antibodies used in opioid screening assays generally cannot discriminate between structurally similar opioids such as hydrocodone (Vicodin), oxycodone (OxyContin), and hydromorphone (Dilaudid), and thus generally cannot distinguish between proper opioid use and abuse of non-prescribed opioids. Chemical structures of some commonly abused opioids are shown in FIG. 11a. The antibodies used in various opioid urine drug test screening assays are cross-reactive toward several off-target molecules including the opioid buprenorphine, which is frequently used to treat opioid addiction, as well as non-opioids including fluoroquinolone antibiotics and the antipsychotic chlorpromazine (see FIG. 11b). This poor selectivity on the part of the antibodies leads to both false-negative and false-positive test results, in turn deterring primary care physicians from implementing urine drug testing for opioids.

EXAMPLES

Example 1

Enzyme-Linked Assay

One split aptamer half having a 3' amine and 5' azide is immobilized covalently on a DNA-BIND 96-well plate (Corning) that is functionalized with NHS esters. The plate is washed with buffer, and excess NHS esters blocked with BSA (attachment, washing, and blocking steps according to manufacturer's instructions). The sample to be tested is added to the wells in the plate along with the second aptamer half bearing a 5' biotin and 3' cyclooctyne. If the small molecule is present in the sample, it will promote ligation of the biotinylated DNA to the DNA strand immobilized on the plate via reaction between the azide and cyclooctyne. The plate is then washed and streptavidin-horseradish conjugate is added.

After again washing, horseradish peroxidase (HRP) substrate (for example, TMB) is added and the results obtained using a UV plate reader.

Example 2

Lateral Flow Assay

The lateral flow biosensor is constructed as described in: Glynou et al., 2003, Oligonucleotide-functionalized gold nanoparticles as probes in a dryreagent strip biosensor for DNA analysis by hybridization. Anal Chem 75:4155-4160, which is incorporated herein by reference. $T_{20}$ DNA-functionalized gold nanoparticles are spotted on a conjugation pad. One split aptamer half is functionalized with a 3' $A_{20}$ sequence and a 5' azide. The second aptamer half is functionalized with a 5' biotin and 3' cyclooctyne. Both aptamer halves are spotted on the conjugation pad just below the gold nanoparticles. The test zone is spotted in one location with streptavidin and in another location with poly-dA DNA.

The lateral flow device is placed in a sample to be tested. If the target small molecule is present, it will promote ligation of the two aptamer halves, generating a DNA molecule having both $A_{20}$ and biotin. This molecule is then bound to the gold nanoparticles as it migrates up the sensor. When the molecules reach the test zone, the biotin will bind to the streptavidin and remaining gold nanoparticles will bind to the poly-dA. The gold nanoparticles are visually observable by their bright red color. If the small molecule is present and has promoted ligation, the gold nanoparticles will form a red line at both the streptavidin and poly-dA test zones, indicating a positive result. If no split aptamer ligation occurs, the gold nanoparticles will not be conjugated to biotin and will thus only form a red line at the poly-dA test zone, indicating a negative test.

Example 3

Cocaine-Dependent Split Aptamer

Figure 12A:
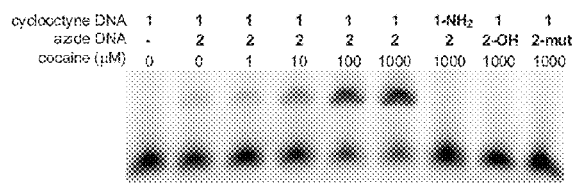
FIG. 12a shows data in accordance with another embodiment of the present invention.
Figure 12B:
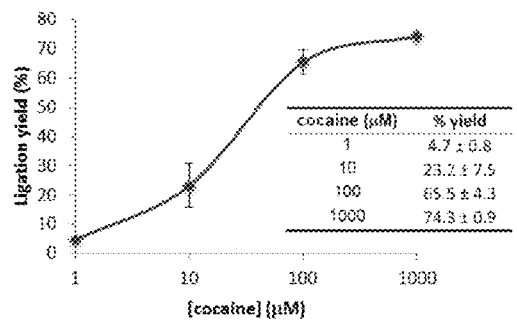
FIG. 12b shows data in accordance with another embodiment of the present invention.

Returning to the discussion of the cocaine-dependent split aptamer case, FIGS. 12a and b show that the templated ligation proceeds in a dose-dependent manner for cocaine concentrations of 1 µM-1 mM, providing ligation yields of 5-74%. FIG. 12a shows a denaturing PAGE of ligation reactions. The lower bands represent unreacted strand 1 and upper bands represent 1+2 ligated product. Conditions for this particular example were 0.5 µM 1, 2.0 µM 2, 25 mM Tris, pH 8.2, 5 mM NaCl, 4 h. FIG. 12b shows yield of ligated product as a function of cocaine concentration. Errors represent standard deviation of three independent trials. As can be seen in FIG. 12, no reaction is observed when the cyclooctyne (1-$NH_2$) or azide (2-OH) is omitted or one base is mutated in the azide strand (2-mut). These controls demonstrate that cocaine-dependent assembly of the split aptamer is sequence-specific and that ligation proceeds via reaction between the azide and cyclooctyne functional groups.

Figure 13:
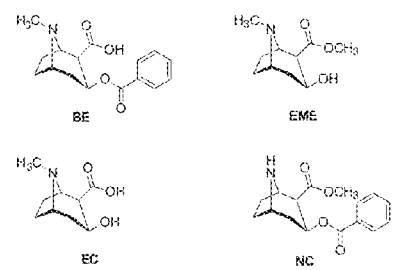
FIG. 13 shows data in accordance with another embodiment of the present invention.
Figure 13:
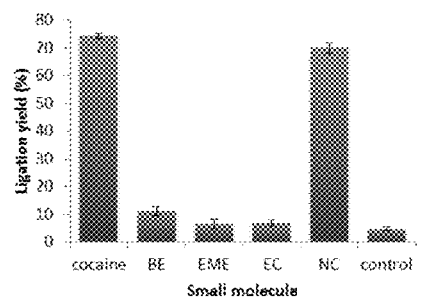

The selectivity of the split aptamer ligation for cocaine versus its structurally similar metabolites is next investigated. Previous studies using the cocaine split aptamer have demonstrated that aptamer assembly is not significantly induced by benzoylecgonine (BE) or ecgonine methyl ester (EME). Binding of ecgonine (EC) by the split aptamer has not been studied, but the regular cocaine aptamer has been shown to selectively bind cocaine over ecgonine. Thus, it is anticipated that the split aptamer ligation would not be strongly promoted by BE, EME, or EC. There appear to be no reports on the selectivity of the cocaine aptamer or split aptamer for the metabolite norcocaine (NC) in which the bridge nitrogen is demethylated. As shown in FIG. 13, reactions using 1 mM BE, EME, or EC result in nominal ligation yields of 11, 7, and 7% respectively. FIG. 13 shows the selectivity of split aptamer ligation for cocaine versus metabolites. Conditions for this particular example are 0.5 μM 1, 2.0 μM 2, 25 mM Tris, pH 8.2, 5 mM NaCl, 1 mM metabolite, 4 h. Control is same conditions as above in FIG. 12, but with no cocaine or metabolite. Error bars represent +/− standard deviation of three independent trials.

This indicates that both the methyl ester and benzoyl group may be necessary for binding of the small molecule to the split aptamer. Interestingly, it is noted that 1 mM NC did in fact promote the ligation reaction, giving a yield of 70%, only 4% less than the yield observed with cocaine. This result suggests that the methyl group of the bridge nitrogen does not play a significant role in recognition of cocaine by the split aptamer. Curiously, the overall tolerance of the split aptamer to cocaine modification is similar to the tolerance of the biological receptors that cocaine targets in vivo, as norcocaine is the only reported cocaine metabolite shown to be pharmacologically active.

Figure 14A:
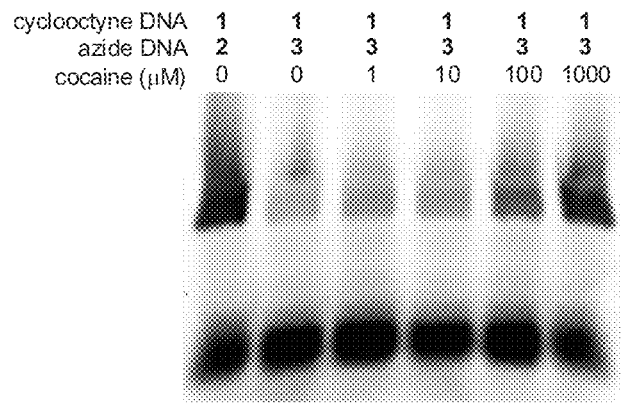
FIG. 14a shows data in accordance with another embodiment of the present invention.

One goal of the present work is the application of small-molecule-dependent split aptamer ligation toward the development of new assays for sensing drug molecules and metabolites in biological samples. Thus, it can be beneficial to establish whether the templated ligation would be compatible with human blood serum. DNA aptamers 1 and 2 are incubated in the same buffered solution used in the experiments above (e.g. 25 mM Tris, pH 8.2, 5 mM NaCl), but having 20% added serum. PAGE analysis reveals significant ligation even in the absence of cocaine (FIG. 14a, lane 1). Earlier studies of the ligation in buffer had revealed that increasing the concentration of NaCl in the reaction mixture led to increasing degrees of background ligation. It is thus hypothesized that higher salt concentrations increase the affinity of the DNA strands for one another such that they can anneal, and subsequently react, even in the absence of the small-molecule target. Given this observation and the fact that sodium ion concentration in normal human serum is 137-147 mM, it is not entirely surprising to observe significant background reaction in 20% serum.

Rather than further dilute the blood serum, it was hypothesized that the split aptamer could be re-engineered to be more "salt tolerant" by converting one or more base pairs to mismatches. This may lower the inherent affinity of the DNA strands, presumably compensating for the increased driving force for annealing that is imparted by the higher salt concentration. Eight azide strands were screened having varying levels of mutation, and it was found that DNA strand 3 (left strand, SEQ ID 006) was sufficiently mutated to drastically reduce the undesired background reactivity yet retain the ability to assemble and react with strand 1 (right strand, SEQ ID 001) in the presence of cocaine (FIG. 14). In strand 3, one GC base pair is mutated to a CC mismatch. However, this negative effect is partially compensated for by mutating a GT wobble pair to a GC base pair. These results speak to the tunability of split aptamer assembly, as only a subtle change to the level of base pairing was necessary to dramatically alter the binding properties of the DNA strands.

Using mutated DNA 3, cocaine dose-dependent ligation is demonstrated with 1 in a sample containing 20% human blood serum (FIG. 14a, lanes 2-6). Interestingly, PAGE does not show any evidence of nuclease degradation of the DNA strands. However, lower yields for the cocaine-dependent ligation are not observed in the buffer-serum mixture compared with buffer alone. This is likely a result of cocaine hydrolysis by serum esterases, as cocaine is known to be rapidly metabolized in vivo to BE and EME, neither of which is capable of promoting the ligation reaction.

Figure 14B:
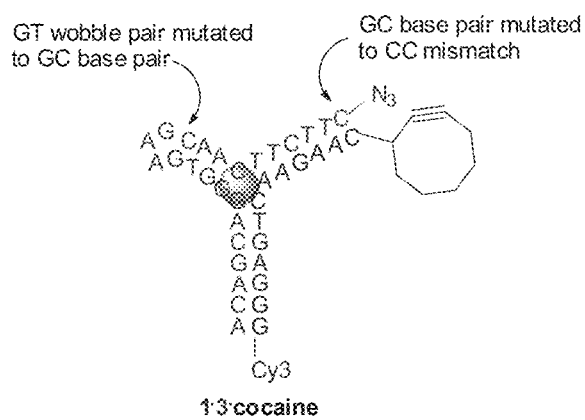
FIG. 14b shows data in accordance with another embodiment of the present invention.

FIG. 14a shows denaturing PAGE of ligation reactions in human blood serum. Conditions for this example are 0.5 μM 1, 2.0 μM 2 or 3, 25 mM Tris, pH 8.2, 5 mM NaCl, 20% serum, 8 h. FIG. 14b shows that the mutant sequence 3 has two mutated bases, which impart a net negative effect on duplex formation with 1.

Using the cocaine split aptamer, it is thus reported here the first example of a DNA-templated reaction that is dependent upon small-molecule binding rather than inherent Watson-Crick affinity. This templated ligation is dose-dependent for cocaine concentrations of 1 μM-1 mM in buffer and 10 μM-1 mM in human blood serum. Studies of the templated reaction under varying conditions has revealed the salt sensitivity of split aptamer assembly, and has enabled the re-engineering of a more "salt tolerant" cocaine split aptamer sequence. Additionally, studies of the split aptamer ligation using cocaine metabolites in which the main functional groups are systematically modified has revealed new insight into the interaction of the split aptamer with cocaine.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. A device for detecting an analyte in a sample, comprising:
   a fluid transfer membrane further including:
   a sample input region operable to receive a liquid sample;
   a reagent region including a first split aptamer segment, a second split aptamer segment, and detection marker, wherein the first and second split aptamers are operable to ligate in the presence of the analyte, and wherein the detection marker is operable to bind to the second split aptamer; and
   a test region having an immobilized binding reagent operable to bind to the first split aptamer segment such that the detection marker is held in the test region when the first split aptamer segment is ligated to the second split aptamer segment due to the analyte being present in the sample;
   wherein the device is arranged such that a sample delivered to the sample input region passes along the fluid transfer membrane through the reagent region prior to contacting the test region.

2. The device of claim 1, further comprising a control region including a control binding reagent operable to bind to the second split aptamer segment.

3. The device of claim 2, wherein the control region is positioned such that the sample contacts the test region prior to contacting the control region.

4. The device of claim 1, further comprising a conjugation region positioned between the reagent region and the test region, wherein the conjugation region is operable to allow ligation of the first and second split aptamers in the presence of the analyte prior to contacting the test region.

5. The device of claim 1, wherein at least one of the first split aptamer, the second split aptamer, or the detection marker is present at the reagent region in a dry form prior to adding the liquid sample to the sample input region.

6. The device of claim 2, wherein the control binding reagent is arranged within the control region to form a discrete control pattern.

7. The device of claim 1, wherein the binding reagent is arranged within the test region to form a discrete test pattern.

8. The device of claim 1, wherein the detection marker includes a member selected from the group consisting of gold nanoparticles, quantum dots, small molecule dyes, colored microbeads, and combinations thereof.

9. A method of detecting an analyte in a sample, comprising:
    applying a liquid sample to a fluid transfer membrane;
    flowing the liquid sample through a reagent region including a first split aptamer segment, a second split aptamer segment, and a detection marker, wherein the first and second split aptamers ligate in the presence of the analyte and the detection marker binds to the second split aptamer; and
    flowing the liquid sample through a test region having an immobilized binding reagent selective for the first split aptamer segment such that the first split aptamer segment binds to the immobilized binding reagent and the detection marker is held in the test region when the first split aptamer segment is ligated to the second split aptamer segment due to the analyte being present in the sample.

10. The method of claim 9, further comprising flowing the liquid sample through a control region including a control binding reagent selective for the second split aptamer segment.

11. The method of claim 10, wherein the liquid sample is passed through the test region prior to contacting the control region.

12. The method of claim 9, further comprising flowing the liquid sample through a conjugation region positioned between the reagent region and the test region, wherein the conjugation region is operable to allow ligation of the first and second split aptamers in the presence of the analyte prior to contacting the test region.

13. The method of claim 9, wherein ligating the first and second split aptamers further includes reacting together:
    the first split aptamer segment having a first reactive group coupled thereto;
    the second split aptamer segment having a second reactive group coupled thereto, wherein the first and second split aptamer segments are collectively selective for the analyte; and
    a sample containing the analyte;
    wherein the first split aptamer segment and the second split aptamer segment bind to the analyte and the first reactive group and the second reactive group react to form an aptamer ligation product of the first split aptamer segment and the second split aptamer segment.

14. The method of claim 9, further comprising detecting the detection marker in the test region.

15. The method of claim 9, wherein at least one of the first or second split aptamer segments is a nucleic acid aptamer.

16. The method of claim 15, wherein the nucleic acid aptamer is a DNA aptamer.

17. The method of claim 9, wherein the liquid sample includes a member selected from the group consisting of urine, blood, plasma, semen, saliva, cerebrospinal fluid, environmental water samples, food and drink samples, and combinations thereof.

18. The method of claim 9, wherein the analyte includes a member selected from the group consisting of narcotics, toxins, and disease biomarkers.

* * * * *